(12) United States Patent
Tashiro et al.

(10) Patent No.: US 8,608,685 B2
(45) Date of Patent: Dec. 17, 2013

(54) BREAST PUMP

(75) Inventors: Mitsuo Tashiro, Tokyo (JP); Shinichi Kataoka, Tokyo (JP)

(73) Assignee: Pigeon Corporation, Tokyo (JP)

( * ) Notice: Subject to any disclaimer, the term of this patent is extended or adjusted under 35 U.S.C. 154(b) by 977 days.

(21) Appl. No.: 12/418,592

(22) Filed: Apr. 4, 2009

(65) Prior Publication Data

US 2009/0254029 A1 Oct. 8, 2009

(30) Foreign Application Priority Data

Apr. 4, 2008 (JP) ................................. 2008-098492

(51) Int. Cl.
*A61M 1/06* (2006.01)

(52) U.S. Cl.
USPC .......................................................... 604/74

(58) Field of Classification Search
USPC .......................................................... 604/74
See application file for complete search history.

(56) References Cited

U.S. PATENT DOCUMENTS

| | | | | |
|---|---|---|---|---|
| 3,032,037 | A * | 5/1962 | Havirco | 604/245 |
| 4,583,970 | A * | 4/1986 | Kirchner | 604/74 |
| 4,759,747 | A * | 7/1988 | Aida et al. | 604/74 |
| 4,813,932 | A * | 3/1989 | Hobbs | 604/74 |
| 4,857,051 | A * | 8/1989 | Larsson | 604/74 |
| 4,883,464 | A * | 11/1989 | Morifuki | 604/74 |
| 4,964,851 | A * | 10/1990 | Larsson | 604/74 |
| 5,007,899 | A * | 4/1991 | Larsson | 604/74 |
| 5,009,638 | A * | 4/1991 | Riedweg et al. | 604/74 |
| 5,071,403 | A * | 12/1991 | Larsson | 604/74 |
| 5,415,632 | A * | 5/1995 | Samson | 604/74 |

(Continued)

FOREIGN PATENT DOCUMENTS

| | | |
|---|---|---|
| CN | 1697664 A | 11/2005 |
| CN | 2834561 Y | 11/2006 |

(Continued)

OTHER PUBLICATIONS

Chinese Office Action for the related Chinese Patent Application No. 200910134014.1 dated Sep. 24, 2012.

(Continued)

*Primary Examiner* — Nicholas Lucchesi
*Assistant Examiner* — Scott Medway
(74) *Attorney, Agent, or Firm* — Kenealy Vaidya LLP

(57) ABSTRACT

A breast pump can be configured to be capable of easily attaching/detaching a primary side serving as a sealed space which is in communication with a milking space and allows the passage of breast milk, with a secondary side in which a case is connected with a pressure changing apparatus. The breast pump can include a breast pump main body connected to the pressure changing apparatus by a conduit, wherein a milking part is disposed so as to liquid-tightly separate a sealed space (or a space that is in fluid communication with the sealed space), and the pressure changing apparatus from each other. A pressure transmission part for transmitting pressure changed by the pressure changing apparatus can be provided. The pressure transmission part can include a deformable part where a volume in the sealed space can be deformed by a pressure fluctuation generated by the pressure changing apparatus. A case can accommodate the deformable part and be connected with the pressure changing apparatus at one end, and the other end of the case can include attachment structure for communicably attaching/detaching the case with the portion of the milking part that forms the sealed space.

16 Claims, 9 Drawing Sheets

(56) References Cited

U.S. PATENT DOCUMENTS

| | | | |
|---|---|---|---|
| 5,749,850 A * | 5/1998 | Williams et al. | 604/74 |
| 5,941,847 A * | 8/1999 | Huber et al. | 604/74 |
| 5,971,952 A * | 10/1999 | Medo | 604/74 |
| 6,042,560 A * | 3/2000 | Niederberger | 604/74 |
| 6,110,141 A | 8/2000 | Nuesch | |
| 6,152,896 A * | 11/2000 | Bachman et al. | 604/74 |
| 6,497,677 B2 * | 12/2002 | Silver | 604/74 |
| 6,663,587 B2 * | 12/2003 | Silver et al. | 604/74 |
| 6,749,582 B2 * | 6/2004 | Britto et al. | 604/74 |
| 7,267,662 B1 * | 9/2007 | Kirchner | 604/74 |
| 7,641,629 B2 * | 1/2010 | Yuen | 604/74 |
| 7,776,008 B2 * | 8/2010 | Renz et al. | 604/74 |
| 7,806,855 B2 * | 10/2010 | Kliegman et al. | 604/74 |
| 8,070,715 B2 * | 12/2011 | Quackenbush et al. | 604/74 |
| 8,070,716 B2 * | 12/2011 | Sutrina et al. | 604/74 |
| 8,100,854 B2 * | 1/2012 | Vogelin et al. | 604/74 |
| 2004/0087898 A1 * | 5/2004 | Weniger | 604/74 |
| 2005/0154348 A1 * | 7/2005 | Lantz et al. | 604/74 |
| 2005/0256449 A1 | 11/2005 | Tashiro | |
| 2007/0179439 A1 * | 8/2007 | Vogelin et al. | 604/74 |
| 2008/0033352 A1 * | 2/2008 | Annis et al. | 604/74 |
| 2010/0121264 A1 * | 5/2010 | Bryan et al. | 604/74 |
| 2010/0262072 A1 | 10/2010 | Attolini et al. | |

FOREIGN PATENT DOCUMENTS

| | | |
|---|---|---|
| GB | 2 299 027 A | 9/1996 |
| JP | 11-226117 A | 8/1999 |
| JP | 3113894 U | 9/2005 |
| JP | 2006-102220 A | 4/2006 |
| JP | 4134335 B2 | 8/2008 |
| JP | 4228396 B2 | 2/2009 |
| JP | 4458292 B2 | 4/2010 |
| JP | 2011-502678 A | 1/2011 |
| JP | 4969034 B2 | 7/2012 |

OTHER PUBLICATIONS

Japanese Office Action for the related Japanese Patent Application No. 2008-098492 dated Nov. 12, 2012.

* cited by examiner

BREAST PUMP

This application claims the priority benefit under 35 U.S.C. §119 of Japanese Patent Application No. 2008-098492 filed on Apr. 4, 2008, which is hereby incorporated in its entirety by reference.

BACKGROUND

1. Technical Field

The presently disclosed subject matter relates to a breast pump for expressing breast milk.

2. Description of the Related Art

A breast pump used by a mother or the like to express breast milk has a horn part that is abutted against a breast, and negative pressure forming means, such as a pump, for creating negative pressure in a space formed by abutting the breast against the horn part. The breast milk suctioned into the negative pressure space is poured into and stored in a bottle. The space formed with the negative pressure is connected with the pump by connection means (see, for example, Japanese Patent Application Publication H11-226117).

Such a breast pump is so designed that a valve body that is accommodated in a housing provided in the connection means is activated by an increase of the liquid level of the breast milk to close an opening that is opened toward the pump side which serves as the negative pressure forming means. In this manner, the breast milk can be prevented from flowing toward the pump which serves as the negative pressure forming means, and thus also prevents rusting and contamination of the mechanical structure. In the case where the negative pressure forming means is constructed not from the pump or other mechanical structure but a manual mechanism such as a lever, the breast milk can be prevented from flowing into this lever and/or onto a user's hand.

However, in this breast pump, the opening that is provided in the connection means and communicates between the negative pressure space and the pump is structured to be closed by the operation of the valve body.

Therefore, because the negative pressure space and the pump are not completely separated in a liquid-tight fashion at all times, there is a risk that the breast milk itself or the breast milk that is formed into a spray by the negative pressure might flow from a small space into the pump, even if/when the valve body closes the opening.

For this reason, the machine parts of the pump may become contaminated, which might result in bacteria development. The manual negative pressure forming means may also become contaminated and unhygienic.

A conventional breast pump is also described in Japanese Patent Application Publication No. 2006-102220.

In this breast pump, a milking part is configured so as to separate a sealed space formed by abutting the milking part against a user's breast when milking (or a space that is in communication with this sealed space) and a pressure changing means from each other in a liquid tight fashion. The milking part has a pressure transmission part for transmitting pressure changed by the pressure changing means, and the pressure transmission part has a deformable part where the cubic content or volume in the sealed space (or the space in communication with the sealed space) is deformed by the movement of the pressure changing means.

Therefore, because the pressure transmission part separates the sealed space formed in the milking part from the pressure changing means (such as a pump) in a liquid tight fashion, the expressed breast milk can be effectively prevented from flowing to the pressure changing means. As a result, the pressure changing means can be prevented from being corroded or damaged by coming into contact with the breast milk, as well as from becoming contaminated and unhygienic.

However, although the breast pump of Japanese Patent Application Publication No. 2006-102220 realizes the structure in which the primary side serving as the sealed space which communicates with a milking space and allows the passage of the breast milk is liquid-tightly separated from the secondary side in which is present a case connected with the pressure changing means, these primary and secondary sides are structurally bonded together.

For this reason, another problem raised is that the bonded structure between the primary side and the secondary side causes inconvenience when carrying, storing, handling, and cleaning.

SUMMARY

According to an aspect of the presently disclosed subject matter a breast pump can be configured to be capable of easily attaching/detaching a primary side which serves as a sealed space and which communicates with a milking space and allows the passage of breast milk, and a secondary side in which a case is connected with pressure changing means. The breast pump can be configured such that is can be handled extremely easily, for example, during cleaning.

In another aspect of the disclosed subject matter, a breast pump can include a substantially conically-shaped milking part abutted against a breast of a user; a breast pump main body having the milking part and attached/detached so as to be communicated with a bottle; and pressure changing means connected with the milking part and alternately generating a negative pressure state and at least an atmosphere pressure state higher than the negative pressure state, wherein the milking part is disposed so as to liquid-tightly separate a sealed space formed by abutting the milking part against the breast of the user when milking, or a space that is communicated with the sealed space, and the pressure changing means from each other, and has a pressure transmission part for transmitting pressure changed by the pressure changing means, the pressure transmission part has a deformable part where a cubic content or volume in the sealed space or the space communicated with the sealed space is deformed by a pressure change generated by the pressure changing means, and a case which accommodates the deformable part and is connected with the pressure changing means at one end, and the other end of the case has attaching/detaching means for communicably attaching/detaching the case and the sealed space.

The pressure transmission means can be configured to change a suction pressure applied to the breast abutted against the milking part, by changing an internal pressure of the sealed space by means of the change in cubic content (volume) of the deformable part accommodated in the case.

Therefore, because the pressure transmission part can completely separate the sealed space formed in the milking part and the pressure changing means such as a pump, expressed breast milk is prevented from flowing from the sealed space to the pressure changing means. Consequently, the pressure changing means can be effectively prevented from being corroded or damaged by coming into contact with the breast milk, as well as from becoming contaminated and unhygienic.

Moreover, the pressure transmission part can include a case connected with the pressure changing means at one end, with the other end having attaching/detaching means for communicably attaching/detaching the case and the sealed space. Therefore, for example, the case accommodating the deformable part can be easily attached/detached to separate it from the sealed space so that not only is it convenient to carry or move the breast pump, but it is also possible to separate and clean only the sealed space which is the primary side that especially requires frequent cleaning.

In a second aspect of the disclosed subject matter, the case can be formed as a cylindrical body for accommodating the deformable part therein, and can include, in the cylindrical body, a tubular projecting part as the attaching/detaching means that projects from an end part corresponding to the other end. The sealed space can have a cylindrical connection part extending into the space, and an inner diameter of the cylindrical connection part can be slightly larger than an outer diameter of the tubular projecting part of the case so that the case and the sealed space are air-tightly joined to each other by inserting the tubular projecting part into the cylindrical connection part.

According to the configuration of the second aspect, because the sealed space is provided with the cylindrical space that has the inner diameter slightly larger than the outer diameter of the tubular projecting part of the case, the pressure changing means and the sealed space can be connected with each other by simply inserting the tubular projecting part into the cylindrical connection part.

In a third aspect of the disclosed subject matter, a periphery of the tubular projecting part of the case can form a flat bottom part. A flat bearing surface can be formed around an opening of the cylindrical connection part of the breast pump main body, and the case and the sealed space can be air-tightly joined to each other by inserting the tubular projecting part into the cylindrical connection part and pushing the flat bottom part of the case until it abuts against the flat bearing surface.

According to the configuration of the third aspect, the periphery of the tubular projecting part of the case can form the flat bottom part. The flat bearing surface can be formed around an opening of the cylindrical connection part of the breast pump main body, and the case and the sealed space can be air-tightly joined to each other extremely easily by simply inserting the tubular projecting part into the cylindrical connection part and pushing the flat bottom part of the case until abutting against the flat bearing surface.

In a fourth aspect of the disclosed subject matter, the cylindrical connection part can be formed to extend substantially vertically toward a lower part of the bottle, with the breast pump main body being placed on the bottle. The tubular projecting part can be formed to gradually taper toward a pointy end.

According to the configuration of the fourth aspect, the tubular projecting part can be aimed downward and inserted into the cylindrical connection part easily due to the configuration of the thin pointy end. By inserting the tubular projecting part deeply, it is brought into close contact with an inner surface of the cylindrical connection part as the outer diameter of the tubular projecting part increases, whereby the tubular projecting part can be fitted to the cylindrical connection part. In this manner, the case and the sealed space can be joined to each other extremely easily.

According to a fifth aspect of the disclosed subject matter, a lid member can cover the one end of the case accommodating the deformable part and to/from which a pipe connected with negative pressure forming means which serves as the pressure changing means is attached/detached. Locking means can be provided for locking the lid member to the sealed space of the breast pump main body at a position where the lid member is installed to the one end of the case, when the case and the sealed space are joined to each other.

According to the configuration of the fifth aspect, the provision of the locking means to the lid member can prevent the case from being released easily from the sealed space.

In a sixth aspect of the disclosed subject matter, the locking means can be provided at a rim part of the lid member and locked to supporting means that projects upward from the breast pump main body.

According to the configuration of the sixth aspect, because the locking means is provided at the rim part of the lid member and locked to the supporting means that projects upward from the breast pump main body, the locking is performed by the locking means at a position other than the joining position between the tubular projecting part and the cylindrical connection part, so that the joining state can be held more stable.

In a seventh aspect of the disclosed subject matter, the locking means which extends from the rim part of the lid member can be locked to a rim part of a bearing surface provided around an opening of the cylindrical connection part of the breast pump main body.

According to the configuration of the seventh aspect, because the lid member can be locked without using the bearing surface provided around the opening of the cylindrical connection part of the breast pump main body, special means for locking the lid member to the breast pump main body is not required, enabling minimization of the breast pump.

As described above, the presently disclosed subject matter can provide a breast pump that is capable of easily attaching/detaching the primary side serving as the sealed space which is in communication with the milking space and allows the passage of breast milk, and the secondary side in which is present the case connected with the pressure changing means. The breast pump can be handled extremely easily when, for example, cleaning the breast pump.

DETAILED DESCRIPTION OF EXEMPLARY EMBODIMENTS

Exemplary embodiments of the presently disclosed subject matter are described hereinafter in detail with reference to the drawings.

Since the embodiments described hereinafter are favorable concrete examples of the presently disclosed subject matter, some technically features are disclosed in detail. However, in the explanation hereinafter, the presently disclosed subject matter should not be considered to be limited to these embodiments or their specific technical features.

Figure 1:
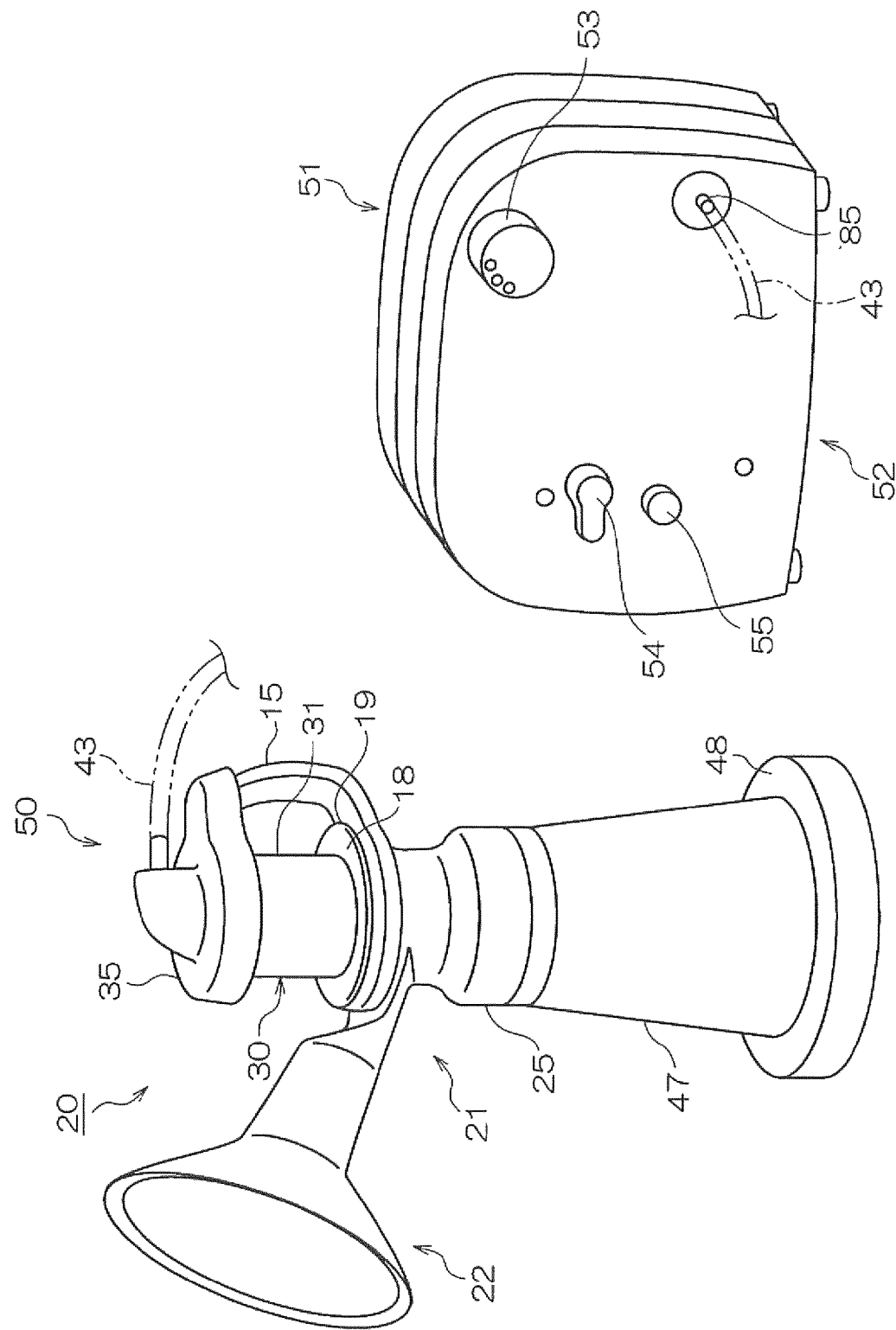
FIG. 1 is a schematic perspective view of an embodiment of a breast pump made in accordance with principles of the disclosed subject matter.

FIG. 1 is a schematic perspective view of an embodiment of a breast pump made in accordance with principles of the disclosed subject matter.

FIG. 1 shows a breast pump 20, wherein the breast pump 20 has a milking unit 50 and a pump unit 51 serving as a pressure changing apparatus connected with the milking unit 50 by a conduit, such as a pipe 43 or other fluid connection tube. The pump unit 51 could also be considered means for changing pressure in the breast pump.

First of all, the milking unit 50 is described.

Figure 2:
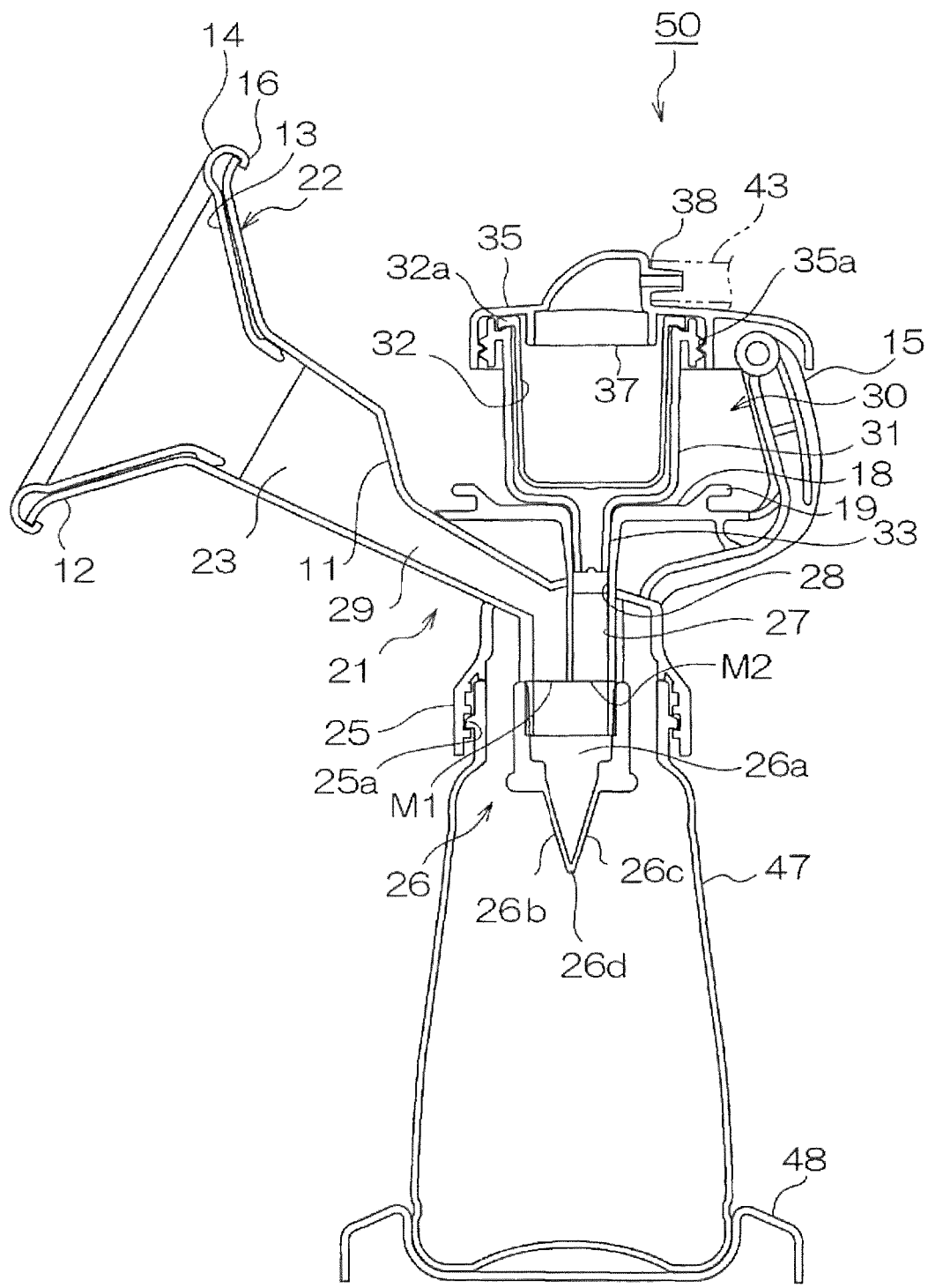
FIG. 2 is a schematic cross-sectional diagram of a milking unit of the breast pump shown in FIG. 1.

FIG. 2 is a schematic cross-sectional diagram of the milking unit 50. In FIGS. 1 and 2, the milking unit 50 has a breast pump main body 21 (to be referred to as "main body" hereinafter) which can be attached/detached to/from a bottle 47 serving as a container for storing expressed breast milk.

The entirety of the main body 21 can be formed by, for example, a relatively light and strong synthetic resin material, such as polycarbonate, polycycloolefin, polyethersulfone, polyamide, polypropylene, and/or other similar materials.

As shown in FIG. 2, the main body 21 has an attaching/detaching part 25 that can be attached/detached to/from the bottle 47 for storing expressed breast milk. The attaching/detaching part 25 can be, for example, a flat cylindrical part having a male screw part 25a therein, which is screwed to a female screw part formed can be formed around the mouth of the bottle 47. Note that the bottle 47 may be used exclusively for the breast pump 20, or a baby bottle or other bottle suitable to the attaching/detaching part 25 may be used. The bottle 47 may be placed on a supporting table 48.

In FIG. 2, an upper part of the attaching/detaching part 25 of the main body 21 is provided with a horn-shaped or conically-shaped milking part 22 that opens outward in an inclined state.

This milking part 22 has an opened passage 11 that opens slightly wider as it extends outward along a central axis to form an air passage 23. An opened pointy end part 12 can be integrally formed at a pointy end of the opened passage 11 so as to open widely into a horn shape. These parts can be formed by the same material as that of the main body 21 and can have relatively high rigidity so as not to be deformed easily, but can also me made from different materials having different rigidity.

A cylindrical pumping mouth deforming member 13 having substantially the same shape as the opened pointy end part 12 can be provided inside the opened pointy end part 12. The pumping mouth deforming member 13 can be attached/detached to/from the opened pointy end part 12. The pumping mouth deforming member 13 can be formed by an elastic body such as silicone rubber, elastomer, natural rubber, and other similar materials.

In addition, a convex stimulation part 14 can be provided at the opened pointy end part 12 of the pumping mouth deforming member 13 to cover the entire opened pointy end part 12.

In use, the convex stimulation part 14 is brought into abutment against a breast when the negative pressure of a sealed space increases, to not only enhance the sealability between the breast and the sealed space, but also to produce a massage effect by pressurizing the breast and applying a favorable stimulus when expressing milk.

The air passage 23 of the milking part 22 serves as an airflow and a passage that allows the passage of the expressed milk. The air passage 23 can be formed in the shape of a cylinder that is gradually opened obliquely upward, and a lower end thereof can be bent downward to the bottle 47 side.

In addition, an opening M1 of the air passage 23 of the milking part 22 can be located inside the attaching/detaching part 25 between the main body 21 and the bottle 47 and attached with a small chamber valve 26. Another air passage 27 can be provided adjacent to the air passage 23.

A lower end opening M2 of the air passage 27 can communicate with the air passage 23 by the small chamber valve 26 as shown in the drawing, while an upper end of the air passage 27 extends upward and can communicate with a pressure transmission apparatus. For example, the upper end of the air passage 27 can communicate with a lower end of a case 31 of a pressure transmission part 30.

Therefore, the inside of the milking part 22, the air passage 23, and the air passage 27 form a sealed space 29 in which is formed negative pressure that suctions the breast milk at the time of expressing the breast milk.

As shown in FIG. 2, the small chamber valve 26 can be in the shape of a cap, the entirety of which can be formed by an elastic body such as silicone rubber, elastomer, natural rubber, or similar materials. Both side walls 26b, 26c shown in FIG. 2 can be elastic inclined walls that gradually approach each other toward lower ends thereof. The lower ends at which the both side walls 26b, 26c came into contact with each other can be provided with a slit 26d. When the expressed breast milk is accumulated in a predetermined amount in a small chamber 26a, the pointy end side of the both side walls 26b, 26c opens as the weight of the accumulated breast milk or the pressure changes with a release of the negative pressure, and consequently the slit 26d opens, thereby dropping the breast milk into the bottle 47, as described hereinafter. Because the slit 26d is formed at the lower ends of the inclined walls, the slit 26d also functions as an air valve for preventing the entry of the air within the bottle 47 into the small chamber 26a when the negative pressure is generated.

At an upper part of the air passage 27 of the main body 21, a cylindrical connection part 28, described hereinafter, can be integrally formed, and an upper part thereof can be formed with a bearing surface 18 along a peripheral part of an opening of the cylindrical connection part 28. The bearing surface 18 can abut or be disposed adjacent the case 31 and can be formed as a dish-like part that is flat or slightly pitted so as to be able to receive a bottom surface of the case 31. A flange part 19 can be formed on an outer rim of the bearing surface 18.

Furthermore, supporting means 15 that projects upward can be formed on the side opposite to a part where the milking part 22 of the main body 21 extends. The supporting means 15 in this embodiment, for example, is a part that extends upward from a side of the bearing surface 18 and forms a projecting body that stands in the form of a pillar or an arm. An upper end of the supporting means 15 reaches the vicinity of an upper end of the case 31 shown in FIG. 2. The case 31 can be supported in a stable manner by the lid member 35 by supporting the lid member 35 of the case 31 by means of the supporting means 15, as described hereinafter.

Figure 3A:
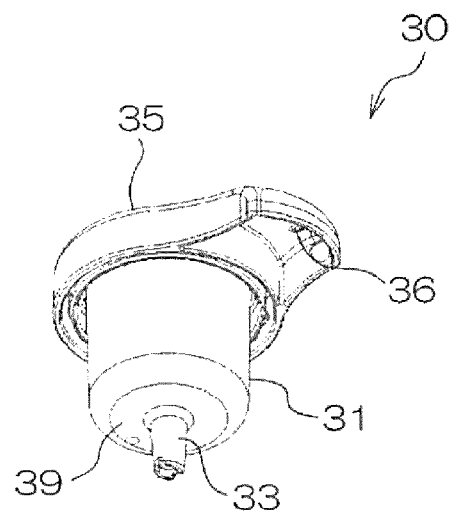
FIGS. 3a and 3b are a perspective view of the lid member of the breast pump shown in FIG. 1, and a perspective exploded view of the lid member of the breast pump shown in FIG. 1, respectively.
Figure 3B:
Figure 3A:
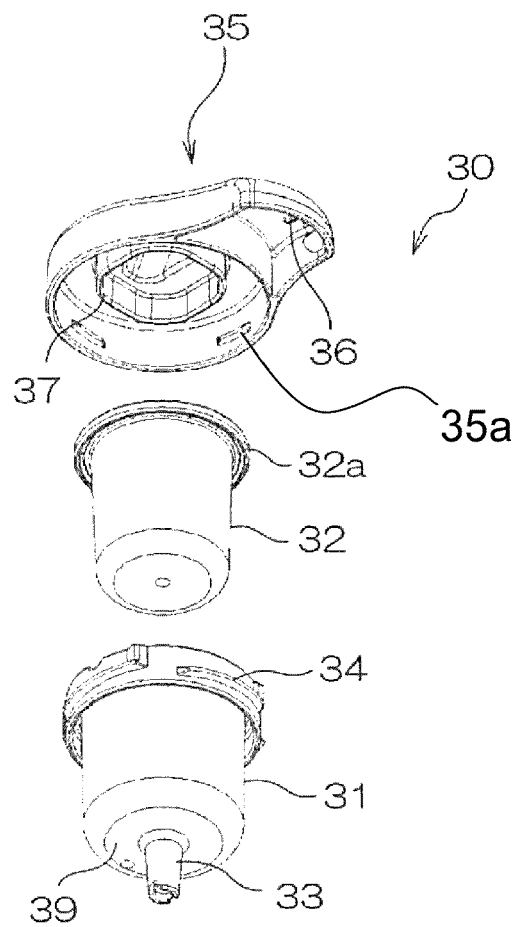

FIG. 3 is a perspective view showing the bottom of the case 31, FIG. 3A showing a state in which the lid member 35 is installed on the case 31, and FIG. 3B being an exploded perspective view.

The case 31 of the pressure transmission part 30 can be, for example, a longitudinally extending cylindrical body having a relatively long internal space extending in the longitudinal direction (or along a central axis) of the cylindrical body, and can be configured to accommodate a deformable part. The deformable part of this embodiment is a member independent from the case 31 and configured as a deforming member 32 attached/detached to/from the case 31.

The deforming member 32 can be formed by an airtight thin material, and can have a flexible property such that it is deformed easily.

Particularly, in this embodiment, the deforming member 32 can be shaped as a cylindrical member that has a bottom and in which, as shown in FIGS. 2 and 3, one end thereof is opened while the other end is closed (to form the bottom). The one end can be brought into internal contact with an inside space of the case 31 that is a cylindrical case formed by hard synthetic resin mold or the like. The deforming member 32 can be made of an elastic body such as silicone, elastomer, natural rubber, or the like, and can be a material that is extremely flexible and has little or no risk of damage by deformation caused by repeated expansion and contraction.

As shown in FIGS. 2 and 3, an opened rim part of an upper end of the deforming member 32 can include an integral flange part 32a which is placed on or abuts a rim part of an upper end opening of the case 31.

An outer rim part of the upper end opening of the case 31 can be formed with attaching/detaching means 34, such as a male screw part, which is screwed to a lower inner periphery 35a of the lid member 35, so that the lid part 35 is attached/detached to/from the case 31 (see FIG. 2).

A rib 37 projecting downward can be provided at a lower end on the inside of the lid member 35.

Therefore, in a state shown in FIG. 2 in which the lid member 35 is screwed and installed into the case 31, the flange part 32a of the deforming member 32 is held in close contact between an upper surface of the opened rim part of the case 31 and a lower surface of the lid member 35. Therefore, the inside of the deforming member 32 is in an airtight state.

An upper end of the lid member 35 of this embodiment can have an attachment part 38 that slightly projects in a lateral direction. By inserting the attachment part 38 into an end part of the flexible pipe 43 as shown in FIG. 1, the attachment part 38 can be attached/detached to/from the pipe 43. In the state shown in FIG. 2, the pipe 43 is in communication with an inside space of the deforming member 32 via the lid member 35. Therefore, this space forms a secondary space that communicates with a pressure changing apparatus via the pipe 43, the pressure changing apparatus being described hereinafter.

This secondary space can be separated from the sealed space 29 in a liquid tight manner by the deforming member 32. The sealed space 29 can be a primary space that includes the air passage 27 continuing from the air passage 23 of the milking part 22 of FIG. 2 and which communicates with the air passage 23 via the small chamber 26a. The inside of the case 31 can connect with the air passage 27 via attaching/detaching means 33 described hereinafter. Specifically, the secondary space is air-tightly and liquid-tightly sealed so that air and liquid do not leak or are at least prevented from leaking.

In addition, at the lower end of the case 31, a central part of a flat bottom part 39 can project vertically downward and can narrow down, to form a hollow cylindrical tubular projecting part 33 serving as the attaching/detaching means, as shown in FIGS. 2 and 3. This tubular projecting part 33 can be formed such that the outer diameter thereof is gradually reduced toward a pointy end.

In relation to this, the cylindrical connection part 28 can be formed in the vicinity of the center of the bearing surface 18 of the main body 21 as shown in FIG. 2. This cylindrical connection part 28 can extend vertically toward the bottle 47 and can communicate with the small chamber 26a. The inner diameter of the cylindrical connection part 28 can be slightly larger than the outer diameter of the tubular projecting part 33 of the case 31 so that, when the tubular projecting part 33 is inserted, the tubular projecting part 33 comes into close external contact with the cylindrical connection part 28, and an airtight state can be maintained.

FIG. 2 shows the above-described state in which the tubular projecting part 33 is fitted into the cylindrical connection part 28, but in a state in which the lid member 35 is installed onto the case 31. A locking structure, such as a locking tab 36 of the lid member 35 is locked to the supporting means 15 to maintain the installation state of the case 31. The locking tab 36 can also be considered a means for locking the lid member 35 with respect to the case 31.

Specifically, an outer peripheral part of the lid member 35 can extend laterally, and the locking tab 36 can be formed as a concaved part, or the like, and can accommodate an upper end of the supporting means 15.

Consequently, not only is it possible to fit the tubular projecting part 33 of the case 31 into the cylindrical connection part 28 in a state in which the lid member 35 is screwed and installed to the upper end of the case 31 accommodating the deforming member 32, but also it is possible to perform the installation simply and support the lid member 35 at two points of the installation part and locking part by causing the locking tab 36 of the lid member 35 to receive a pointy end of the supporting means 15, whereby the installation state can be maintained.

The pump unit 51 serving as the pressure changing apparatus is described next.

FIG. 1 shows a schematic perspective view of the pump unit 51.

As described with regard to FIG. 1, the pump unit 51 can be connected with the milking unit 50 by the flexible pipe 43. The pump unit 51 can serve as a vacuum pump and can be configured such that when a switch described hereinafter is turned on, the secondary space of the milking unit 50 (e.g., the inside of the case 31 of the pressure transmission part 30), and the space that communicates therewith can be suctioned to negative pressure. In this case, formation of negative pressure can be realized in a pulsed condition on the basis of a structure described hereinafter. In other words, pressure fluctuation for obtaining pulsation is performed in which the pressure is fluctuated continuously from a negative pressure state to at least an atmosphere pressure state.

In FIG. 1, a chassis 52 of the pump unit 51 can include an on/off switch (knob) 54 for turning the drive of the pump unit 51 on/off and a cycle knob 55 for adjusting a pulsation period when forming negative pressure. In addition, a finger grip 53 for adjusting the magnitude of the negative pressure can be provided, and the flexible pipe 43 can be attached to the chassis 52.

Figure 4:
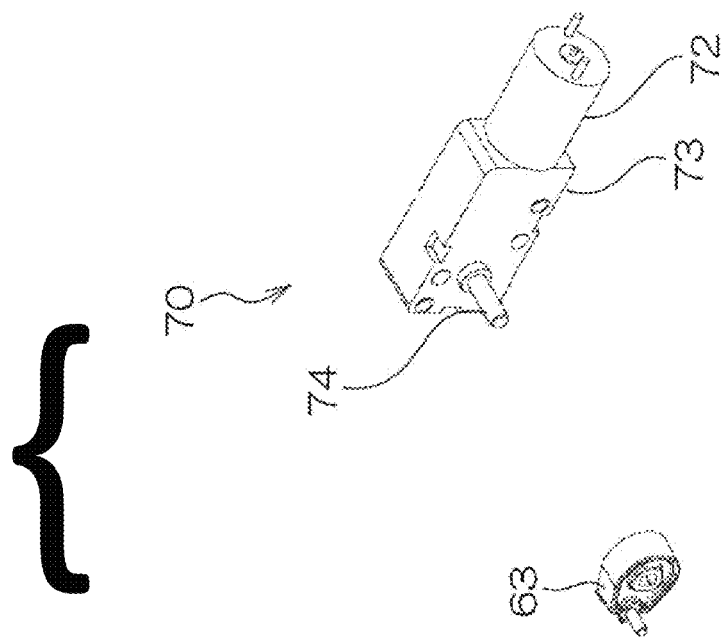
FIG. 4 is an exploded perspective view of a motor part of the breast pump shown in FIG. 1.
Figure 5:
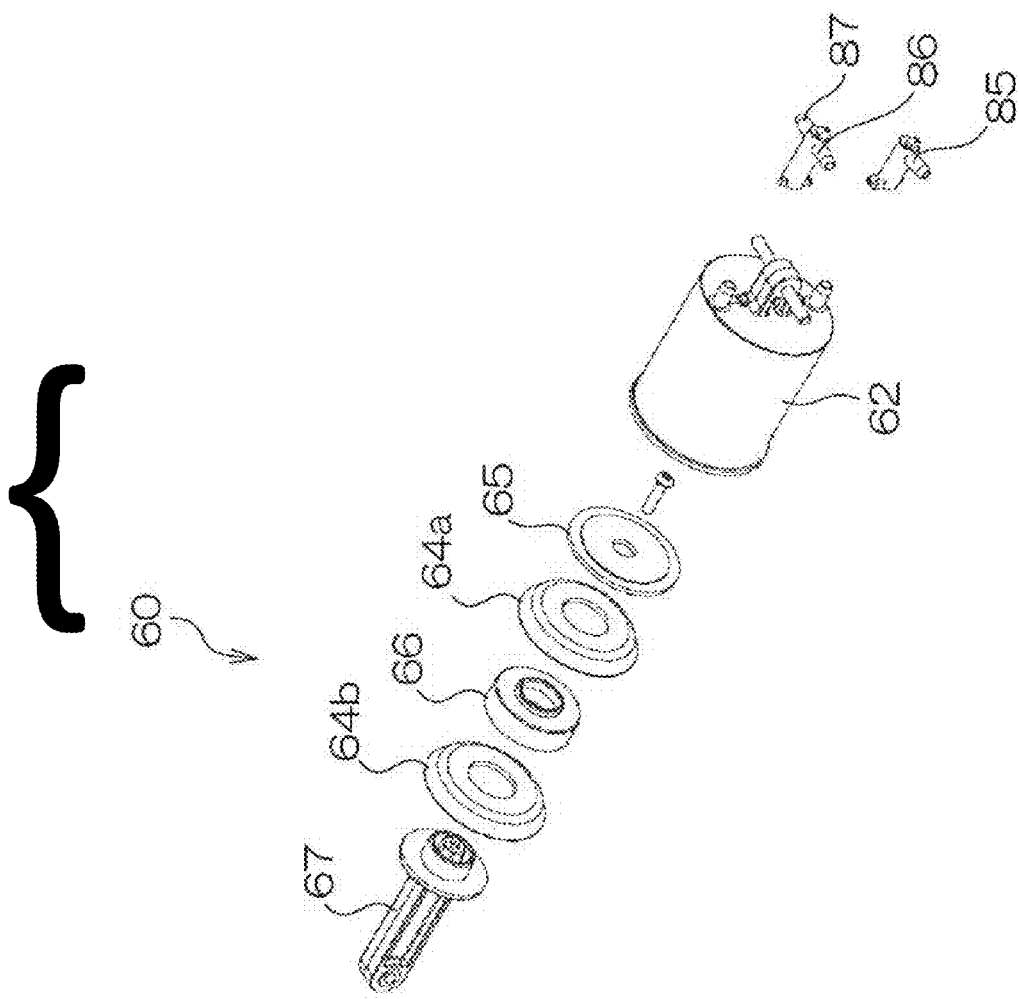
FIG. 5 is an exploded perspective view of a piston part of the breast pump shown in FIG. 1.
Figure 6:
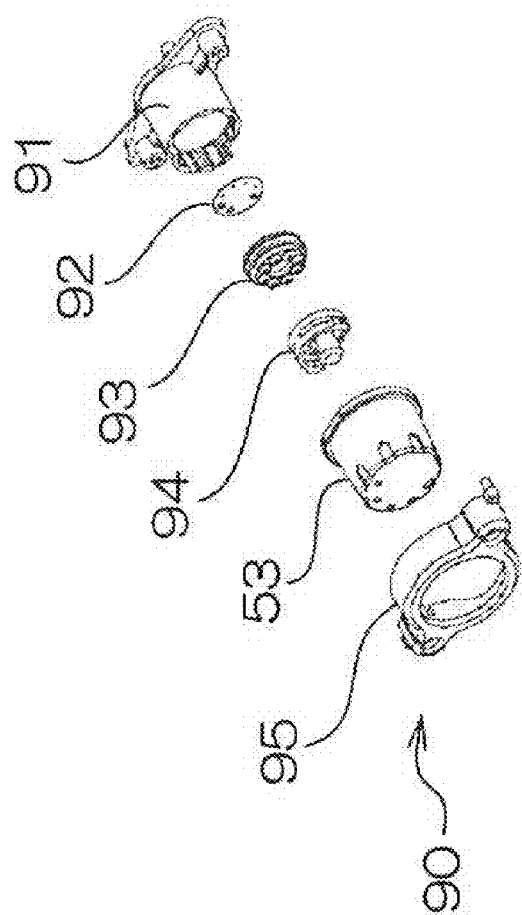
FIG. 6 is an exploded perspective view of a pressure adjusting part of the breast pump shown in FIG. 1.

FIGS. 4 to 6 show a chassis 52 of the pump unit 51 accommodating a motor part 70, cylinder part 60, pressure adjusting part 90, and the like.

The motor part 70 can include a motor 72 and a gear unit 73 to which the shaft of the motor 72 is bonded. A continuous current motor can be used as the motor 72 in this embodiment.

In the gear unit 73, a drive shaft 74 for appropriately decelerating and transmitting the rotation of the shaft of the motor extends and can be connected with an eccentric cam 63. A camshaft of the eccentric cam 63 can be connected with a piston rod of the cylinder part 60 to convert the rotational motion of the drive shaft 74 to reciprocal motion of the piston rod.

Specifically, the cylinder part 60 can include a cylinder 62, and the piston rod 67 can be inserted in an advanceable/retractable manner into the cylinder 62. Two piston rings 64a, 64b having a spacer 66 therebetween can be attached to the piston head of the piston rod 67, and a fixing plate 65 can be used to fix them with screws.

A suction tube 85, exhaust tube 86, and pressure adjusting tube 87 can communicate with the inside of the cylinder 62. Consequently, when the piston rod 67 is reciprocated, a predetermined valve is driven, and negative pressure is formed within the cylinder 62, which is transmitted via the suction tube 85.

Here, selecting proper materials for the piston rings 64a, 64b can reduce slide resistance of the piston rod 67 that is generated within the cylinder 62, as well as a power loss, so that energy conservation can be achieved and the sealing characteristics can be improved.

Therefore, the piston rings 64a, 64b can be formed by Teflon™, nylon, polyacetal, or other material with relatively excellent heat resistance and low slide resistance, and can have an outer diameter that is slightly larger than the inner diameter of the cylinder, and can be configured to form a piston fin. A flanged outer rim part of the piston fin that abuts against an inner wall of the cylinder 62 can be deformed as the piston rod 67 reciprocates.

Teflon™ can be selected as the material for the piston rings 64a, 64b, in order to reduce the slide resistance of the piston rod 67 within the cylinder 62 and improve the sealing characteristics.

However, a disadvantage of Teflon™ is its high production cost, since it cannot be created using a die.

In the present embodiment, therefore, these piston rings 64a, 64b can be formed using a polyacetal mold. In this manner, the slide resistance of the piston rod 67 within the cylinder 62 as well as the power loss can be reduced so that a reduction of the production cost can be realized while achieving energy conservation and improving the sealing characteristics.

The exhaust tube 86 can be connected with an exhaust valve. The suction tube 85 can be exposed from the chassis 52 via a tube attachment opening and connected with the elastic pipe 43 and with the lid member 35 of the milking unit 50, as shown in FIG. 1. The pressure adjusting tube 87 can be connected with the pressure adjusting part 90.

A control circuit board can be stored in the chassis 52, which is fixed and supported in, for example, a storage unit. The control circuit board controls the drive of the pump unit 51 and can be connected with the on/off switch (knob) 54 of the pump unit 51 and the cycle knob 55 for adjusting a pulsation period when forming negative pressure.

The pressure adjusting part 90 can communicate with the cylinder 62 of the cylinder part 60 and can have a storage case 91 for storing parts. The storage case 91 can have therein a plate 92 that has a large-diameter negative pressure adjusting hole and a small-diameter negative pressure adjusting hole to adjust the negative pressure within the cylinder 62. These holes of the plate 92 are switched over by rotating the plate 92. The plate 92 can be fixed to the finger grip 53 via a cushion 93 and a spinning piece 94.

The breast pump 20 according to the present embodiment can be configured as described above, wherein the on/off switch knob 54 of the pump unit 51 shown in FIG. 1 can be operated to activate the pump unit 51, and whereby the motor 72 is actuated/rotated, the drive shaft 74 is rotated via the gear unit 73, and the obtained rotational motion is converted to the reciprocal motion of the piston rod 67 within the cylinder 62 via the eccentric cam 63. The negative pressure that is formed within the cylinder 62 by the reciprocal motion of the piston rod can be pulsated, changed, and transmitted to the pressure transmission part 30 of the shown milking unit 50 via the suction tube 85 and the elastic pipe 43.

In this manner, the pressure inside the deforming member 32 within the case 31 can be reduced in FIG. 2. Therefore, the internal space of the deforming member 32 is deformed in the case 31 in such a way as to be crushed by the difference in pressure between the inside of the deforming member 32 and the space outside the deforming member 32, whereby the bottom part of the deforming member 32 rises and approaches the lid member 35. Specifically, because the volume of the deforming member 32 is reduced significantly in the case 31, the pressure in the sealed space 29 that communicates with the space of the case 31 outside the deforming member 32 is reduced significantly.

In other words, because the negative pressure increases within the sealed space 29, breast milk is suctioned from the breast, and the expressed breast milk falls into the small chamber 26a through the air passage 23. Moreover, at this moment, the convex stimulation part 14 of the pumping mouth deforming member 13 is deformed on the breast side by the pressure difference and pressurizes and stimulates the breast, promoting the secretion of the breast milk.

Next, when the negative pressure state is released by the reciprocal motion of the cylinder rod 67 of the pump unit 51, the deforming member 32 is displaced again so as to restore its condition, as shown in FIG. 2. As a result, the volume of the deforming member 32 increases within the case 31, whereby the pressure in the sealed space is increased and the pressure for suctioning the breast milk is reduced.

By repeating the above-described operation, the operation of the pump unit 51 serving as the pressure changing apparatus is transmitted to the sealed space 29 by the movement of the deforming member 32 of the pressure transmitting part 30. Consequently, the pressure of the sealed space 29 is increased or decreased so that a state similar to the action of feeding an infant can be realized, and the expressed breast milk can be accumulated in the bottle 47.

When negative pressure acts through the pipe 43 in the above operation, the deforming member 32 is contracted and deformed in such a way as to stick to the lid member 35. At this moment, the contracted and deformed deforming member 32 trying to stick to the lid member 35 can be stopped from sticking completely by the presence of the rib 37.

The pressure transmission part 30 has the case 31, the upper end of the case can be connected with the pump unit 51 via the lid member 35, and the lower end of the case 31 can have the attaching/detaching means 33 for communicably attaching/detaching the case 31 and the sealed space 29 to/from each other. Therefore, for example, the case 31 accommodating the deforming part 32 can be easily attached/detached to separate it from the sealed space 29 so that not only is it convenient to carry or move the breast pump but also it becomes possible to separate and clean only the sealed space 29 which is the primary portion that especially requires frequent cleaning.

Accordingly, it is possible to easily attach/detach a primary side serving as the sealed space 29 which communicates with the milking space and allows the passage of breast milk, and a secondary side including the case 31 connected with the pump unit 51 serving as pressure changing apparatus, thereby making it extremely easy to handle the breast pump when, for example, cleaning the breast pump.

Moreover, because the pressure transmission part 30 can be configured to completely separate, liquid-tightly and air-tightly, the sealed space 29 formed in the milking part 22 from the pressure changing apparatus such as the pump, the breast milk itself or spray breast milk that is accumulated in the sealed space, that is, the small chamber 26a or the like, can be effectively prevented from flowing into the pump unit 51. As a result, the pressure changing apparatus such as the pump unit 51 or other pressure changing means can be prevented from being corroded or damaged by coming into contact with the breast milk, as well as from becoming contaminated and unhygienic.

In addition, in the present embodiment, the case 31 is formed as a cylindrical body for accommodating the deforming member 32 therein, and has, in the cylindrical body, the tubular projecting part 33 as the attaching/detaching means.

Also, the sealed space 29 can include the cylindrical connection part 28 extending into to the sealed space 29, and the inner diameter of the cylindrical connection part 28 can be made slightly larger than the outer diameter of the tubular projecting part 33 so that the case 31 and the sealed space 29 can be air-tightly joined to each other by inserting the tubular projecting part 33 into the cylindrical connection part 28.

As a result, the pump unit 51 and the sealed space 29 can be connected with each other by simply inserting the tubular projecting part 33 into the cylindrical connection part 28.

As described above, the periphery of the tubular projecting part 33 of the case 31 can be configured to form a flat bottom part, and the flat bearing surface 18 can be formed around the opening of the cylindrical connection part 28 of the main body 21. Therefore, the case 31 and the sealed space 29 can be air-tightly joined to each other extremely easily by inserting the tubular projecting part 33 into the cylindrical connection part 28 and pushing the flat bottom part of the case 31 until abutting against the flat bearing surface 18.

In addition, the cylindrical connection part 28 can be formed to extend substantially vertically toward the lower part of the bottle 47, with the bottle 47 being placed as shown in FIG. 2, and the tubular projecting part 33 can be formed to gradually taper toward the pointy end.

Therefore, the tubular projecting part 33 can be aimed downward and inserted into the cylindrical connection part 28 easily due to the thin pointy end. By inserting the tubular projecting part 33 deeply, it is brought into close contact with the inner surface of the cylindrical connection part 28 as the outer diameter of the tubular projecting part 33 increases, whereby the tubular projecting part 33 can be fitted to the cylindrical connection part 28. In this manner, the case 31 and the sealed space 29 can be joined to each other extremely easily.

Furthermore, this embodiment has the lid member 35 that covers the upper end of the case 31 accommodating the deforming part 32 and to/from which the pipe 43 connected with the pump unit 51 which serves as the negative pressure forming means is attached/detached.

Because this embodiment can also include the locking tab 36 for locking the lid member 35 to the sealed space 29 of the main body 21 at a position where the lid member 35 is installed onto the upper end of the case 31 when the case 31 and the sealed space 29 are joined to each other, the joining state between the case 31 and the sealed space 29 can be stably supported so that the case 31 can be prevented from being released easily.

In addition, in this embodiment, the locking tab 36 shown in FIG. 3 can be provided at the rim part of the lid member 35. The locking tab 36 can be locked to the supporting means 15 projecting upward from the main body 21, as described in FIG. 2.

Therefore, the locking can be performed by the locking means at a position other than the joining position between the tubular projecting part 33 and the cylindrical connection part 28 so that the joining state can be held more stable.

Figure 7:
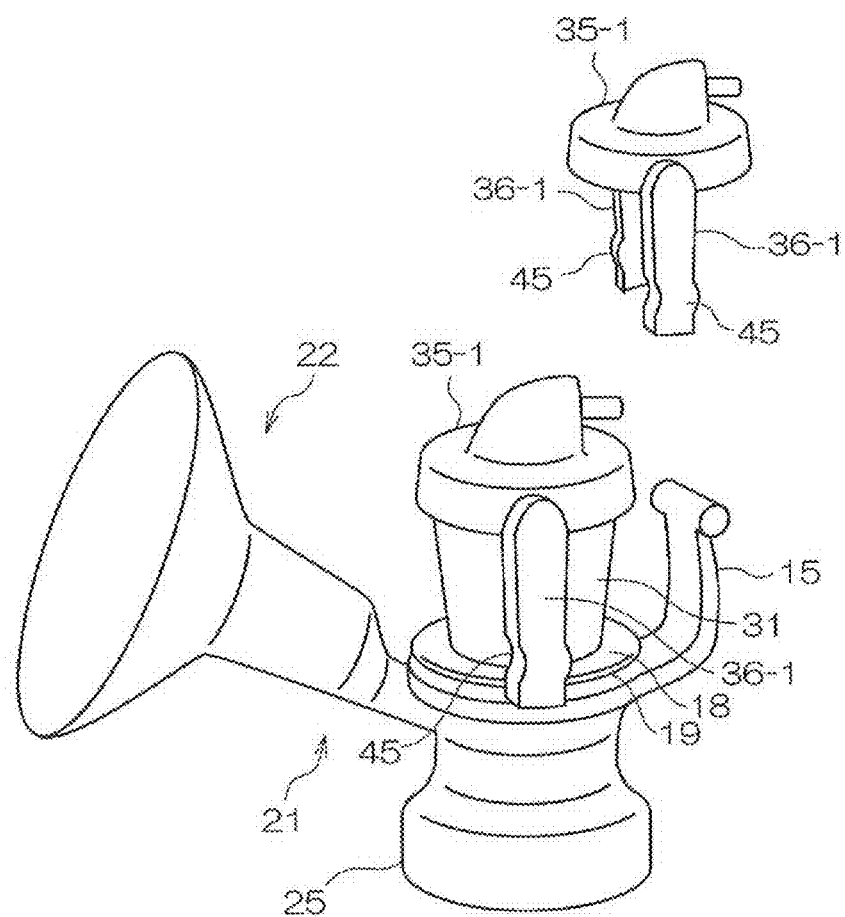
FIG. 7 is an explanatory diagram of Modification 1 of the breast pump shown in FIG. 1.
Figure 8:
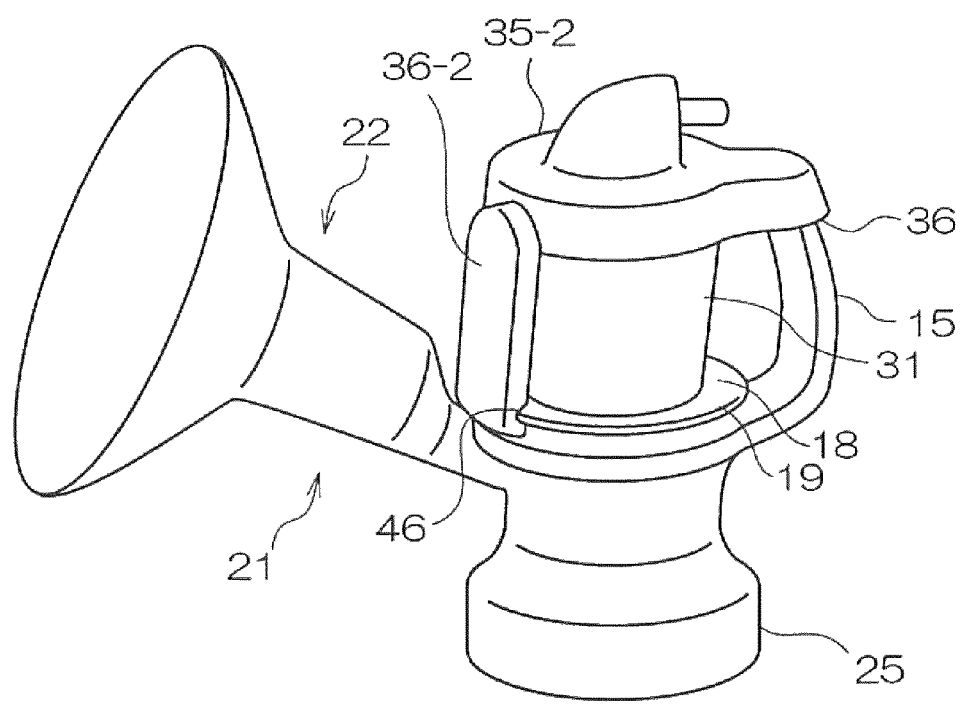
FIG. 8 is an explanatory diagram of Modification 2 of the breast pump shown in FIG. 1.

FIGS. 7 and 8 show modifications of the locking member provided in the lid member.

FIG. 7 shows a first modification, wherein the configuration of the lid member is slightly different from the configuration shown in FIG. 3.

In this example, an outer rim of a lid member 35-1 has a pair of leg pieces 36-1 extending downward. The leg pieces 36-1 can be deformed in a direction in which they approach/separate from each other on the basis of a predetermined elasticity. A hook-shaped locking part 45 is formed in the vicinity of a lower end of each of the leg pieces 36-1.

Therefore, when the lid member 35-1 is lifted down to cover the case 31 as shown in the lower part of FIG. 7, the leg pieces 36-1 come into contact with the flange part 19 of the bearing surface 18, the leg pieces 36-1 are slightly opened to be positioned outside the outer rim of the flange part 19, and the flange part 19 enters the locking members 45 of the respective leg pieces 36-1 and is then locked.

FIG. 8 shows the second modification, wherein the configuration of the lid member is slightly different from the configuration shown in FIG. 3.

In this example, a lid member 35-2 is formed with not only the same locking tab 36 as that of the lid member 35 shown in FIG. 3, but also a leg piece 36-2 that is obtained by stretching an end part outer rim on the opposite side downward. A hook-shaped locking part 46 is formed at a lower end part of this leg piece 36-2.

Accordingly, the lid member 35-2 is locked to the flange part 19 by the locking part 46 and also to the supporting means 15.

Thus, according to each of the modifications, the locking is performed by the locking means at a position other than the joining position between the tubular projecting part and the cylindrical connection part, so that the joining state can be held more stable. In addition, because the lid member can be locked using the bearing surface 18 provided around the opening of the cylindrical connection part of the main body 21, no special means for locking the lid member to the main body 21 is required, enabling minimization of the breast pump.

FIG. 9 shows a substantial part of the second embodiment, wherein the configurations other than the illustrated configurations are the same as those of the first embodiment. Therefore, the differences between these configurations are described.

Figure 9A:
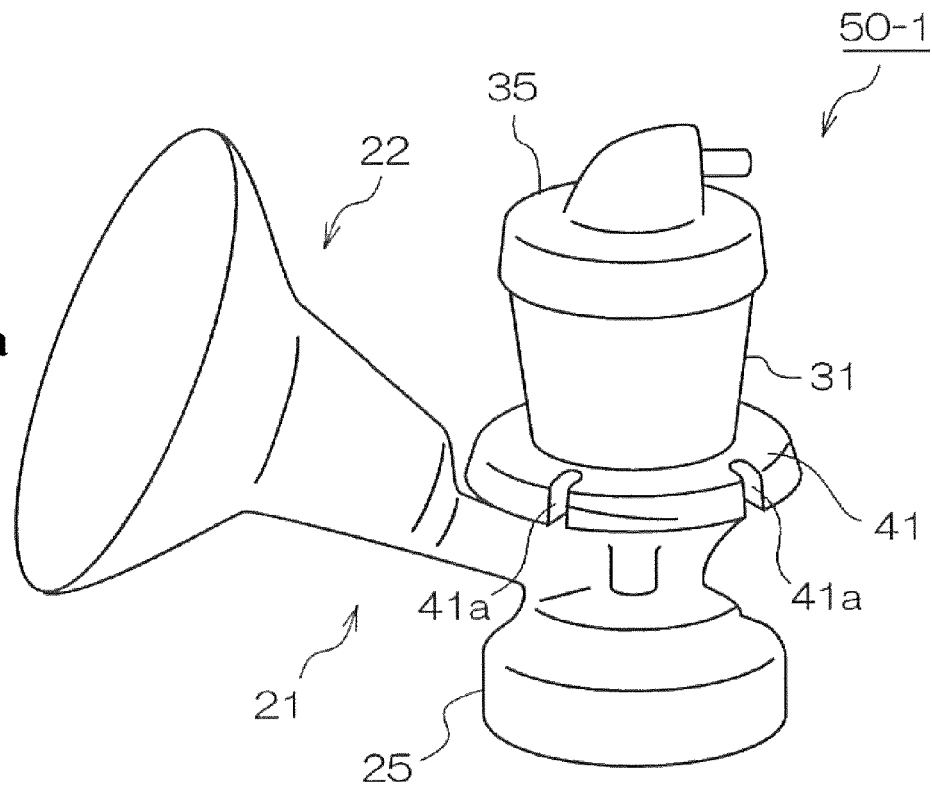
FIGS. 9a and 9b are a partial perspective view and a partial cross section view, respectively, of another embodiment of a breast pump made in accordance with principles of the disclosed subject matter.
Figure 9B:
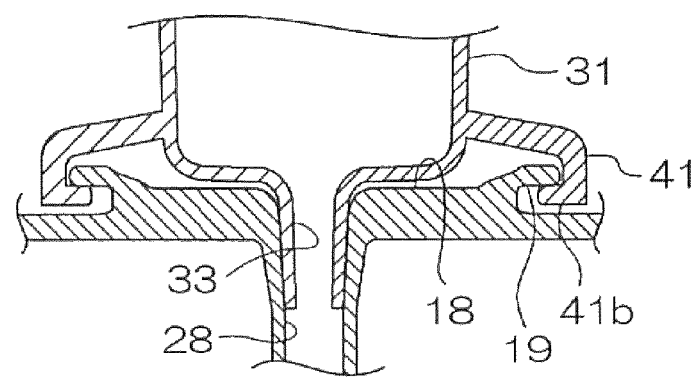

In FIG. 9A, the case 31 is attached/detached to/from the main body 21 of a milking unit 50-1. A lower end part of the case 31 forms a flanged locking means 41 that bulges radially, as shown in FIG. 9B.

Specifically, the locking means 41 has a step part 41b, a rim part of which that bulges in the form of a flange is bent downward and a pointy end of the same faces inward. The pointy end of the flange part 19 of the bearing surface 18 can be locked to the step part.

As shown in FIG. 9A, a plurality of slits 41a are formed in the locking means 41 in a circumferential direction thereof so that the locking means 41 can be elastically deformed. As shown in FIG. 9B, the flange part 19 of the bearing surface 18 is fitted to deform the locking means 41 easily, so that the case can be attached/detached.

The present embodiment configured as described above not only can produce the operational effects similar to those of the first embodiment, but also can form the locking means for supporting the joining state of the case 31 without using the supporting means 15 shown in FIG. 2.

Therefore, the joint stability similar to that of the first embodiment can be realized without the supporting means 15 shown in FIG. 2.

The present invention is not intended to be limited to the above embodiments.

For example, the deforming member accommodated in the case 31 may be configured integrally with the case to obtain "a deforming part" as a part of this configuration.

The deforming part can take not only a simple bottomed cylindrical body but also various patterns including a cornice structure.

The tubular projecting part 33 serving as the attaching/detaching means can be appropriately changed to have a shape and structure different from those described in the embodiments.

Note that each configuration of each of the embodiments and modifications described above may be omitted or combined with other structures that are not described herein, if necessary.

What is claimed is:

1. A breast pump, comprising:
a substantially conically-shaped milking part configured to abut against a breast of a user;
a breast pump main body configured to be attached to and detached from a bottle; and
a pressure changing apparatus connected with the milking part and configured to alternately generate a first negative pressure state in the milking part and a second negative pressure state having a less negative pressure value than the first negative pressure state in the milking part,
wherein the milking part is disposed so as to liquid-tightly separate the pressure changing apparatus from a sealed space in the milking part formed when the milking part abuts against the breast of the user during milking, and the milking part includes a pressure transmission apparatus configured to transmit pressure changed by the pressure changing apparatus to the sealed space, the pressure transmission apparatus having a deformable part configured to change a volume of the sealed space when the deformable part is deformed by a pressure change generated by the pressure changing apparatus, the deformable part including an elastic material that defines an air tight expandable volume and which separates the sealed space from the pressure changing apparatus in a liquid-tight manner, and
the pressure transmission apparatus having a case which accommodates the deformable part and is connected with the pressure changing apparatus at one end, and includes attachment structure at an other end of the case configured to communicably attach the case with a portion of the milking part that defines the sealed space, wherein
the case is configured to accommodate the deformable part therein, and the attachment structure includes a tubular projecting part, the tubular projecting part projecting from the other end of the case, and the milking part includes a cylindrical connection part extending into the sealed space, and an inner diameter of the cylindrical connection part is slightly larger than an outer diameter of the tubular projecting part of the case so that the case and the sealed space are air-tightly joined to each other when the tubular projecting part is inserted into the cylindrical connection part.

2. The breast pump according to claim 1, wherein the case is a cylindrical body and the tubular projecting part is adjacent the cylindrical body.

3. The breast pump according to claim 2, wherein a periphery of the tubular projecting part of the case forms a flat bottom part, a flat bearing surface is formed around an opening of the cylindrical connection part, and the case and the sealed space of the milking part are air-tightly joined to each other when the tubular projecting part is fully inserted into the cylindrical connection part such that the flat bottom part of the case abuts against the flat bearing surface.

4. The breast pump according to claim 3, wherein the cylindrical connection part extends substantially vertically toward a lower part of the breast pump main body that is configured for attachment to the bottle, and wherein the tubular projecting part gradually tapers toward a pointy end.

5. The breast pump according to claim 1, further comprising a lid member that covers the one end of the case accommodating the deformable part, the lid member being connected to a conduit connected with the pressure changing apparatus, and the lid member including a locking structure configured to lock the lid member to the case to thus form the sealed space.

6. The breast pump according to claim 2, further comprising a lid member that covers the one end of the case accommodating the deformable part, the lid member being connected to a conduit connected with the pressure changing apparatus, and the lid member including a locking structure configured to lock the lid member to the case to thus form the sealed space.

7. The breast pump according to claim 3, further comprising a lid member that covers the one end of the case accommodating the deformable part, the lid member being connected to a conduit connected with the pressure changing apparatus, and the lid member including a locking structure configured to lock the lid member to the case to thus form the sealed space.

8. The breast pump according to claim 4, further comprising a lid member that covers the one end of the case accommodating the deformable part, the lid member being connected to a conduit connected with the pressure changing apparatus, and the lid member including a locking structure configured to lock the lid member to the case to thus form the sealed space.

9. The breast pump according to claim 5, wherein the lid member includes a rim part, and the locking structure is located at the rim part of the lid member and locked to a supporting structure that projects upward from the breast pump main body.

10. The breast pump according to claim 6, wherein the lid member includes a rim part, and the locking structure is located at the rim part of the lid member and locked to a supporting structure that projects upward from the breast pump main body.

11. The breast pump according to claim 7, wherein the lid member includes a rim part, and the locking structure is located at the rim part of the lid member and locked to a supporting structure that projects upward from the breast pump main body.

12. The breast pump according to claim 8, wherein the lid member includes a rim part, and the locking structure is located at the rim part of the lid member and locked to a supporting structure that projects upward from the breast pump main body.

13. The breast pump according to claim 5, wherein the locking structure extends from a rim part of the lid member and is locked to a rim part of a bearing surface provided around an opening of the cylindrical connection part.

14. The breast pump according to claim 6, wherein the locking structure extends from a rim part of the lid member and is locked to a rim part of a bearing surface provided around an opening of the cylindrical connection part.

15. The breast pump according to claim 7, wherein the locking structure extends from a rim part of the lid member and is locked to a rim part of a bearing surface provided around an opening of the cylindrical connection part.

16. The breast pump according to claim 8, wherein the locking structure extends from a rim part of the lid member and is locked to a rim part of a bearing surface provided around an opening of the cylindrical connection part.

* * * * *